United States Patent
Ziv-Ari et al.

(10) Patent No.: US 8,998,812 B2
(45) Date of Patent: Apr. 7, 2015

(54) ULTRASOUND METHOD AND PROBE FOR ELECTROMAGNETIC NOISE CANCELLATION

(75) Inventors: Morris Ziv-Ari, Tirat Carmel (IL); Alexander Sokulin, Tirat Carmel (IL); Eitan Berg, Tirat Carmel (IL)

(73) Assignee: General Electric Company, Schenectady, NY (US)

( * ) Notice: Subject to any disclaimer, the term of this patent is extended or adjusted under 35 U.S.C. 154(b) by 633 days.

(21) Appl. No.: 12/880,410

(22) Filed: Sep. 13, 2010

(65) Prior Publication Data

US 2012/0065509 A1    Mar. 15, 2012

(51) Int. Cl.
*A61B 8/00* (2006.01)
*A61B 8/08* (2006.01)
*G01S 7/52* (2006.01)
*G01S 15/89* (2006.01)
*G06T 5/00* (2006.01)
*A61B 18/12* (2006.01)

(52) U.S. Cl.
CPC .............. *A61B 8/4444* (2013.01); *A61B 8/5207* (2013.01); *A61B 8/5269* (2013.01); *G01S 7/52023* (2013.01); *G01S 7/52077* (2013.01); *G01S 15/899* (2013.01); *G06T 5/002* (2013.01); *G06T 2207/10132* (2013.01); *A61B 2018/1293* (2013.01)

(58) Field of Classification Search
None
See application file for complete search history.

(56) References Cited

U.S. PATENT DOCUMENTS

| | | | |
|---|---|---|---|
| 3,982,426 A | 9/1976 | Newhouse et al. | |
| 4,542,657 A | 9/1985 | Barber et al. | |
| 5,183,048 A | 2/1993 | Eberle | |
| 6,102,859 A | 8/2000 | Mo | |
| 6,293,912 B1 | 9/2001 | Sorensen | |
| 6,633,658 B1 | 10/2003 | Dabney et al. | |
| 2005/0025377 A1 | 2/2005 | Avinash et al. | |
| 2005/0033166 A1* | 2/2005 | Hastings et al. | 600/437 |
| 2005/0131299 A1 | 6/2005 | Robinson et al. | |
| 2007/0213615 A1* | 9/2007 | McLaughlin et al. | 600/447 |
| 2009/0141957 A1* | 6/2009 | Yen et al. | 382/131 |
| 2011/0245676 A1* | 10/2011 | Lin et al. | 600/447 |

FOREIGN PATENT DOCUMENTS

| | | |
|---|---|---|
| JP | H0663044 A | 3/1994 |
| JP | 2002291735 A | 10/2002 |
| JP | 2006158732 A | 6/2006 |
| JP | 200926144 A | 11/2009 |

(Continued)

OTHER PUBLICATIONS

Unofficial translation of CN Office Action and Search Report from CN Application No. 2011102835631 dated Apr. 25, 2014.

(Continued)

*Primary Examiner* — Christopher Cook
(74) *Attorney, Agent, or Firm* — Dean Small; The Small Patent Law Group LLC

(57) ABSTRACT

A method of ultrasound imaging includes acquiring ultrasound data with a plurality of transducer elements. The ultrasound data includes a plurality of signals. The method includes detecting an electromagnetic noise signal during the process of acquiring the ultrasound data. The method also includes modifying the plurality of signals based on the electromagnetic noise signal to generate a plurality of noise-cancelled signals.

18 Claims, 4 Drawing Sheets

(56) References Cited

FOREIGN PATENT DOCUMENTS

| KR | 100823102 B1 | 4/2008 |
|---|---|---|
| WO | 2012/066472 A1 | 5/2012 |

OTHER PUBLICATIONS

Ma, Zhimin, "Identification of Ultrasonic echo signal and Inhibition of Interference", Engineering Journal of Wuhan University Issue 05, Oct. 30, 1992 pp. 534-537.

Luo, Yongfen et al. "Detection and Pre-Processing of Partial Discharge Ultrasonic Signals" Journal of Xi'an Jiaotong University Issue 08, Aug. 20, 2006, pp. 964-968.

Unofficial translation of abstract MA, Zhimin "Identification of Ultrasonic echo signal and Inhibition of Interference" Applied Acoustics Issue 06, Dec. 31, 1993 pp. 22-25.

Unofficial translation of French Search Report and Written Opinion from FR Application No. 1157918 dated Dec. 31, 2013.

\* cited by examiner

ULTRASOUND METHOD AND PROBE FOR ELECTROMAGNETIC NOISE CANCELLATION

FIELD OF THE INVENTION

This disclosure relates generally to ultrasound imaging and specifically to a method and ultrasound probe for removing electromagnetic noise from ultrasound data.

BACKGROUND OF THE INVENTION

A conventional ultrasound imaging system comprises an array of transducer elements for transmitting an ultrasound beam and receiving a reflected ultrasound beam from the object being studied. By selecting the phase delay and amplitude of the applied voltages, the individual transducer elements can be controlled to produce ultrasonic waves which combine to form a net ultrasonic wave that travels along a preferred vector direction and is focused at a selected point along the beam. Multiple firings may be used to acquire data representing the same anatomical information. The beamforming parameters of each of the firings may be varied to provide a change in focus or otherwise change the content of the received data for each firing, e.g., by transmitting successive beams along the same line with the focal point of each beam being shifted relative to the focal point of the previous beam. By changing the phase rotation and amplitude of the input voltages provided to the transducer elements, the ultrasound beam may be moved to scan the object.

The same principles apply when the array is employed to receive the reflected ultrasound energy. A receive beamformer typically focuses the transducer elements in the array on a focal point while receiving ultrasound energy. As with the transmission mode, this focused reception of the ultrasonic energy is achieved by imparting a separate phase delay and gain to the signal from each of the receiving transducer elements.

When acquiring ultrasound data, such as in B-mode imaging, conventional ultrasound imaging systems typically transmit an ultrasound beam focused at a single focal point positioned along the line. Then, the transducer elements detect reflected ultrasonic signals. After transmitting the ultrasound beam, the transducer elements are used to detect samples of the reflected ultrasound beam at different points in time. Acquiring each of the samples may use some or all of the transducer elements. Additionally, each of the samples corresponds to a different time or depth along the line. The transducer elements of a conventional ultrasound system typically convert the ultrasound energy into electrical signals. The electrical signals, in turn, are sent to a receive beamformer where the appropriate phase delays and gains are applied to each of the electrical signals in order to "focus" the transducer array on the correct depth for the received ultrasound signal. The beamformer typically adjusts the focus of the array so that the transducer elements are focused on the appropriate depth for the sample being acquired. After beamforming, the electrical signals acquired at a particular point or sample are combined into a signal indicative of the acoustic reflectivity of the object at a specific point along the line. In order to generate an image, a processor typically maps the amplitude of signals from the beamformer to a gray scale for display on a monitor or other display device.

One problem with conventional ultrasound imaging systems is that they are particularly sensitive to electromagnetic noise. Any external or internal electromagnetic noise may alter electric signals from the transducer elements and/or the beamformer. If left uncorrected, electromagnetic noise may cause artifacts in ultrasound images. For example, external electromagnetic noise which is coherent across channels, often results in images with central regions showing increased pixel intensity. This region of increased pixel intensity is sometimes referred to as a "flashlight artifact" because the region of brightness resembles the beam of a flashlight. The effects of random noise, or noise that changes significantly over a short period of time, is harder to characterize, but might still result in images with pixel values that are not indicative of the received ultrasound signal.

Conventional ultrasound imaging systems have taken steps to isolate the ultrasound imaging systems from electromagnetic noise. For instance, they have employed various types of shielding, including Faraday cages, in an attempt to minimize the electromagnetic noise in the ultrasound imaging system. However, such isolation techniques are typically less than perfect and, in noisy environments, significant electromagnetic noise may still penetrate into the system. Electromagnetic noise may be particularly problematic when a strong electromagnetic source, such as an RF, or Bovie, knife, is operating is close proximity to the ultrasound imaging system.

For these and other reasons there is a need for an improved method and ultrasound probe for ultrasound imaging.

BRIEF DESCRIPTION OF THE INVENTION

The above-mentioned shortcomings, disadvantages and problems are addressed herein which will be understood by reading and understanding the following specification.

In an embodiment, a method of ultrasound imaging includes acquiring ultrasound data with a plurality of transducer elements. The ultrasound data includes a plurality of signals. The method includes analyzing the ultrasound data to determine an estimated electromagnetic noise signal. The method also includes modifying the plurality of signals based on the estimated electromagnetic noise signal to generate a plurality of noise-cancelled signals, where the plurality of noise-cancelled signals contains less electromagnetic noise than the plurality of signals.

In another embodiment, a method of ultrasound imaging includes acquiring ultrasound data with a plurality of transducer elements. The ultrasound data includes a plurality of signals. The method includes detecting an electromagnetic noise signal with a sensor during the process of acquiring the ultrasound data. The method includes modifying the plurality of signals based on the electromagnetic noise signal to generate a plurality of noise-cancelled signals, where the plurality of noise-cancelled signals contains less noise than the plurality of signals.

In another embodiment, an ultrasound probe includes a housing and a transducer element attached to the housing. The transducer element is adapted to receive ultrasonic energy and generate a signal based on the ultrasonic energy. The probe also includes a sensor attached to the housing. The sensor is adapted to detect electromagnetic noise and transmit an electromagnetic noise signal based on the detected electromagnetic noise.

Various other features, objects, and advantages of the invention will be made apparent to those skilled in the art from the accompanying drawings and detailed description thereof.

DETAILED DESCRIPTION OF THE INVENTION

In the following detailed description, reference is made to the accompanying drawings that form a part hereof, and in which is shown by way of illustration specific embodiments that may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken as limiting the scope of the invention.

Figure 1:
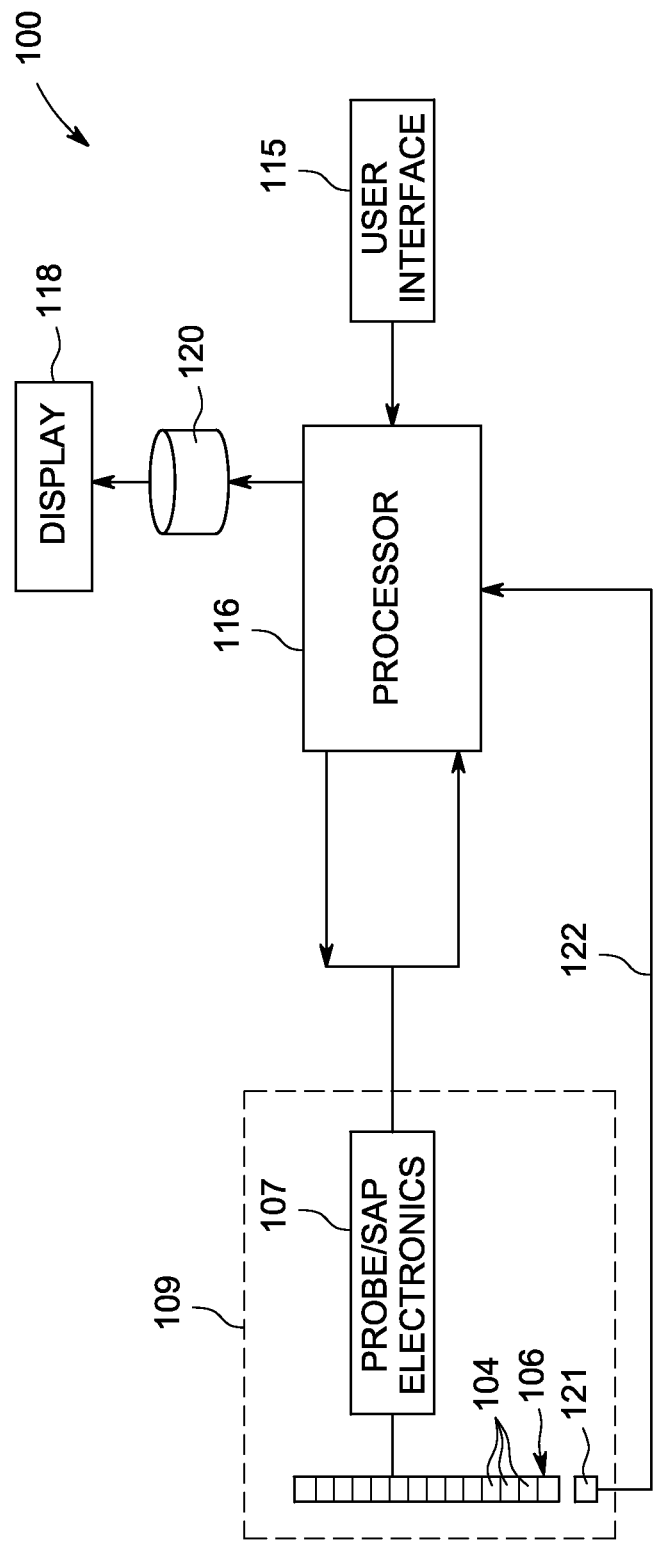
FIG. 1 is a schematic diagram of an ultrasound imaging system in accordance with an embodiment.

FIG. 1 is a schematic diagram of an ultrasound imaging system 100. The ultrasound imaging system 100 includes an ultrasound probe 109, a user interface 115, a processor 116, a memory 120, and a display 118. The ultrasound probe 109 includes a plurality of transducer elements 104 arranged in a transducer array 106, and probe/sub-aperture processor (SAP) electronics 107, hereinafter probe/SAP electronics 107. While the schematic diagram of FIG. 1 only shows 10 transducer elements 104 in the transducer array 106, it should be appreciated that other embodiments may have transducer arrays with significantly more transducer elements. Also, a variety of geometries of transducer arrays may be used. The probe/SAP electronics 107 may be used to control the switching of the elements 104. The probe/SAP electronics 107 may also be used to group the elements 104 into one or more sub-apertures. According to an embodiment, the processor 116 may perform the transmit beamforming on the signals that are sent to the transducer array 106. The transmit beamforming applies the appropriate time delays to the transducer elements 104 in the transducer array in order to focus the ultrasound beam at the intended location. The processor 116 may also perform receive beamforming on the signals from the transducer array 106. Other embodiments may use separate dedicated components to perform one or both of the transmit beamforming and the receive beamforming. The transducer elements 104 in the transducer array 106 emit ultrasonic signals into the tissue of the patient being examined. The ultrasonic signals are back-scattered from structures in the body, like blood cells or muscular tissue, to produce echoes that return to the elements 104. The echoes are converted into electrical signals, or ultrasound data, by the elements 104 and the electrical signals are received by the processor 116. For purposes of this disclosure, the term ultrasound data may include the processed or unprocessed data that was acquired by an ultrasound imaging system. The electrical signals may be processed to remove electromagnetic noise by the processor 116, forming noise-cancelled signals. Then the processor 116 may apply beamforming to the noise-cancelled signals. Details about the removal of electromagnetic noise will be discussed in detail hereinafter. The user interface 115 may be used to control operation of the ultrasound imaging system 100, including, to control the input of patient data, to change a scanning or display parameter, and the like.

The processor 116 may also be used to process the ultrasound data and prepare frames of ultrasound information for display on the display 118. The processor 116 may be adapted to perform one or more processing operations on the ultrasound information according to a plurality of selectable ultrasound modalities. The ultrasound information may be processed in real-time during a scanning session as the echo signals are received. For the purposes of this disclosure, the term "real-time" is defined to include a procedure that is performed without any intentional delay. Additionally or alternatively, the ultrasound information may be stored temporarily in a buffer (not shown) during a scanning session and processed in less than real-time in a live or off-line operation. Some embodiments of the invention may include multiple processors (not shown) to handle the processing tasks. For example, a first processor may be utilized to demodulate and decimate the ultrasound signal while a second processor may be used to further process the data prior to displaying an image. It should be appreciated that other embodiments may use a different arrangement of processors.

According to an embodiment, the ultrasound probe 109 of ultrasound imaging system 100 may optionally include a sensor 121. Other embodiments may include probes with multiple sensors. The sensor 121 may be connected to the processor 116 by an electrical connection 122. The sensor 121 is adapted to detect an electromagnetic noise signal while the transducer array 106 is detecting ultrasonic energy. The sensor 121 is connected to the processor 116, so that the processor 116 may use the information regarding the electromagnetic noise signal when processing signals from the transducer array 106. The sensor 121 is shown as being adjacent to the transducer array 104. However, in other embodiments, the sensor 121 may be located elsewhere on an ultrasound probe. The sensor 121 will be described in more detail hereinafter.

Still referring to FIG. 1, the ultrasound imaging system 100 may continuously acquire ultrasound information at a frame rate of, for example, 20 Hz to 60 Hz. However, other embodiments may acquire ultrasound information at a different rate. For example, some embodiments may acquire ultrasound information at a rate slower than 20 Hz while other embodiments may acquire ultrasound information at a rate faster than 60 Hz. A memory 120 is included for storing processed frames of acquired ultrasound information that are not scheduled to be displayed immediately. In an exemplary embodiment, the memory 120 is of sufficient capacity to store at least several seconds worth of frames of ultrasound information. The frames of ultrasound information are stored in a manner to facilitate retrieval thereof according to its order or time of acquisition. The memory 120 may comprise any known data storage medium.

Optionally, embodiments of the present invention may be implemented utilizing contrast agents. Contrast imaging generates enhanced images of anatomical structures and blood flow in a body when using ultrasound contrast agents including microbubbles. After acquiring ultrasound data while using a contrast agent, the image analysis includes separating harmonic and linear components, enhancing the harmonic component and generating an ultrasound image by utilizing the enhanced harmonic component. Separation of harmonic components from the received signals is performed using suitable filters. The use of contrast agents for ultrasound imaging is well-known by those skilled in the art and will therefore not be described in further detail.

In various embodiments of the present invention, ultrasound information may be processed by other or different mode-related modules (e.g., B-mode, Color Doppler, power Doppler, M-mode, spectral Doppler anatomical M-mode, strain, strain rate, and the like) to form 2D or 3D data sets of image frames and the like. For example, one or more modules may generate B-mode, color Doppler, power Doppler, M-mode, anatomical M-mode, strain, strain rate, spectral Doppler image frames and combinations thereof, and the like. The image frames are stored and timing information indicating a time at which the image frame was acquired in memory may be recorded with each image frame. The modules may include, for example, a scan conversion module to perform scan conversion operations to convert the image frames from Polar to Cartesian coordinates. A video processor module may be provided that reads the image frames from a memory and displays the image frames in real time while a procedure is being carried out on a patient. A video processor module may store the image frames in an image memory, from which the images are read and displayed.

Figure 2:
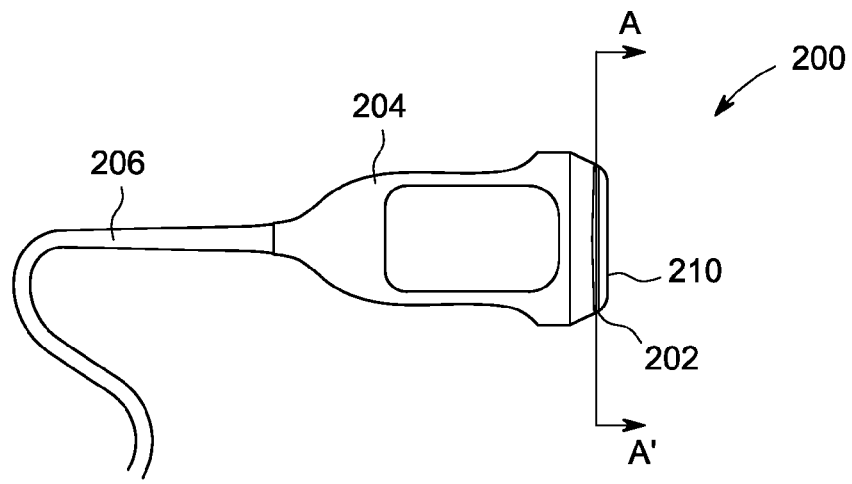
FIG. 2 is a schematic representation of an ultrasound probe in accordance with an embodiment.

Referring to FIG. 2, a schematic representation of an ultrasound probe is shown in accordance with an embodiment. The ultrasound probe 200 includes a transducer array 202 disposed in a housing 204. A cord 206 is attached to the housing 204.

Figure 3:
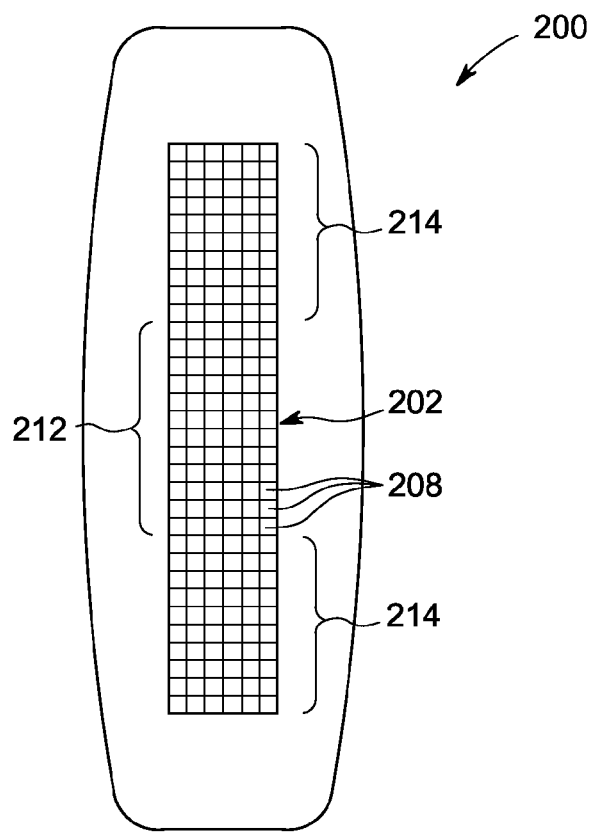
FIG. 3 is a schematic representation of a sectional view of an ultrasound probe in accordance with an embodiment.

FIG. 3 is a schematic representation of a sectional view of the ultrasound probe 200 along the line A-A' according to an embodiment. Common components will be labeled with the same reference number in both FIG. 2 and FIG. 3.

Referring to both FIG. 2 and FIG. 3, the transducer array 202 may be a linear array comprising 192 transducer elements 208. According to an embodiment, the transducer elements 208 may be arranged in a grid that is 6 transducer elements wide by 32 transducer elements tall. It should be appreciated by those skilled in the art that additional embodiments might include transducer arrays of different arrangements. For example, additional embodiments may use transducer arrays including a curved transducer array, a matrix transducer array, and a mechanical 3D transducer array depending upon the intended use of the probe.

The transducer array 202 is positioned behind an acoustic lens 210 that is used to help shape ultrasound waves that are emitted from the transducer array 202. The transducer elements 208 are divided into a central region 212, and a pair of edge regions 214. According to the embodiment shown, the central region 212 includes the 12 rows of elements in the center and the edge regions 214 include the 10 rows of elements on either side of the central region 212. During most imaging modes of phased array probes, the phase delays applied to the transducer elements in the central region 212 are all relatively similar. By comparison, due to their distance from the central region 212, the transducer elements in the edge regions 214 may have significantly different phase delays applied to the signals from each of the elements. It should be appreciated by those skilled in the art that the exact size of the edge regions 214 may vary depending upon the type of transducer and the selected imaging mode. For purposes of this disclosure, the edge regions may include one or more regions that are positioned away from the center of the transducer array. The edge regions may also include two or more regions separated from each other by a central region, or an edge region may form a continuous ring or rectangular frame around a central region in a matrix probe.

Figure 4:
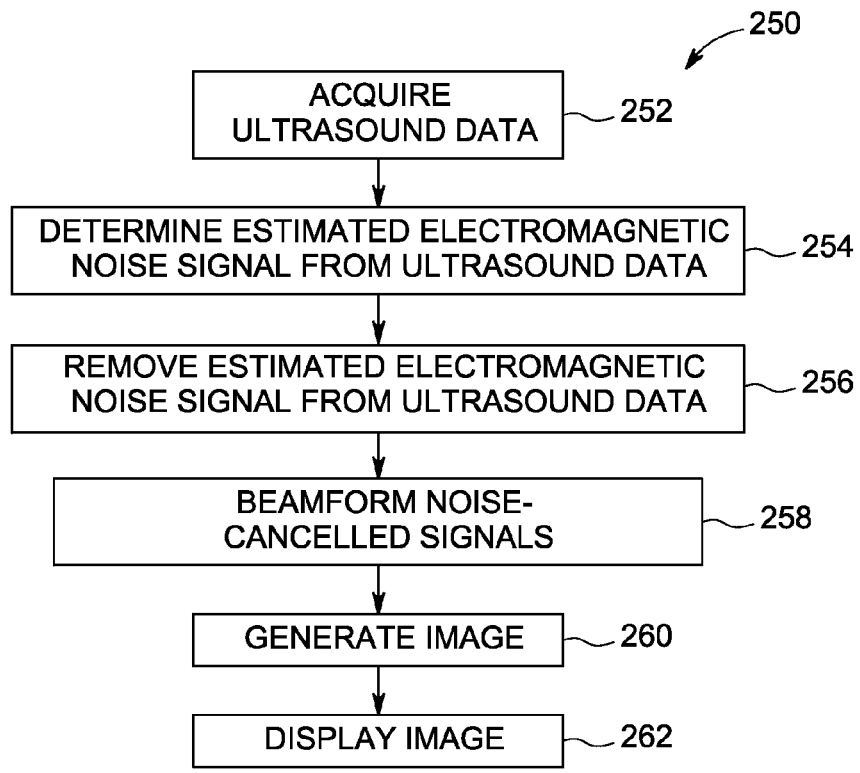
FIG. 4 is a flow chart illustrating a method in accordance with an embodiment.

FIG. 4 is a flow chart illustrating a method 250 in accordance with an embodiment. An ultrasound imaging system such as the ultrasound imaging system 100 (shown in FIG. 1) may be used to perform the method 250. The individual blocks 252, 254, 256, 258, 260, and 262 represent steps that may be performed in accordance with the method 250. The technical effect of the method 250 is the display of images with reduced electromagnetic noise.

According to an exemplary embodiment, the method 250 may be performed with the ultrasound imaging system 100 (shown in FIG. 1) modified so that the probe 109 is replaced with the probe 200 from FIGS. 2 and 3. Other than the probe, the ultrasound imaging system of the exemplary embodiment includes the same components as the ultrasound imaging system 100. Common reference numbers will be used to describe common components between the ultrasound imaging system used in the exemplary embodiment and the ultrasound imaging system 100 shown in FIG. 1. According to the exemplary embodiment, at step 252, the processor 116 (shown in FIG. 1) controls the acquisition of ultrasound data. According to the embodiment shown in FIG. 3, each transducer element 208 (shown in FIG. 3) may be mapped to a single channel when receiving ultrasound data. However, according to other embodiments, groups of transducer elements 208 may be mapped to each channel. Also, it should be appreciated that other embodiments may use multiple processors to perform various tasks instead of just the processor 116 as shown in ultrasound imaging system 100. The process of acquiring ultrasound data was described hereinabove, so it will not be described again in detail.

Referring to FIG. 4, at step 254, the processor 116 (shown in FIG. 1) analyzes the ultrasound data. According to an embodiment, the processor 116 may analyze the ultrasound data in order to identify coherent noise, such as electromagnetic noise. Since coherent noise does not change significantly with location, coherent noise will affect ultrasound data in each of the channels in substantially the same manner.

Referring now to FIGS. 1, 2, and 3, as described above, the portion of the signal from a coherent noise source may be assumed to be substantially the same in each of the channels. However, as described hereinabove, signals from transducer elements in the central region 212 typically have relatively minor phase delays applied to them during receive beamforming. In contrast, the phase delays applied to the signals from the transducer elements in the edge regions 214 are substantially more varied in most imaging modes. Regardless of the phase delay to the signals, the coherent noise signal, such as an electromagnetic noise signal, arrives at substantially the same time in each of the channels. Therefore, it is possible to extract the electromagnetic noise component through the use of a cross-correlation technique, such as averaging. According to an exemplary embodiment, the signals from all of the transducer elements in the edge regions 214 may be averaged together. Since ultrasound signals from the same position arrive to the edge regions 214 with more significant phase delay differences, the ultrasound signal component either drops out or it is not strongly represented in the resulting average. However, since, as described above, the electromagnetic component phase is generally the same in each of the channels, the resulting average is strongly representative of the electromagnetic noise signal. The processor 116 may then use the average signal as an estimated electromagnetic noise signal. Those skilled in the art will appreciate that this exemplary technique may only work well on coherent noise sources. Additionally, other embodiments may use cross-correlation techniques other than averaging in order to identify an estimated electromagnetic noise signal. It will also be apparent that other embodiments may use less than all of the channels from the edge regions 214 for the calculation of the estimated noise signal. Also, some embodiments may use signals from several of the channels connected to elements in the central region 212. However, for the embodiment that uses averaging as the cross-correlation technique, it is important that the average is not based strongly on signals from the central region or else there is a risk of including the ultrasound data as part of the estimated electromagnetic noise signal.

At step 256, the processor 116 removes the estimated electromagnetic noise signal from the ultrasound data. According to an exemplary embodiment, the estimated electromagnetic noise signal may be processed before the processor 116 removes the estimated electromagnetic noise signal from the ultrasound data. For example, the estimated electromagnetic noise signal may be filtered to create a "smoother" waveform and scaled in proportion to the channel that is being modified. For example, the estimated electromagnetic noise signal may be scaled based on the gain applied to a signal from a specific element or channel. However, other embodiments may perform additional processing of the estimated electromagnetic noise signal, including applying a phase delay to the electromagnetic noise signal that is specific to the channel. However, according to yet other embodiments, the processor may remove an unprocessed estimated electromagnetic noise signal from the ultrasound data.

Still referring to FIGS. 1, 2, and 3, the processor 116 may subtract the estimated electromagnetic noise signal (either unprocessed or after processing) from each of the signals from the transducer array 202. It should be appreciated that the estimated electromagnetic noise signal may be subtracted from ultrasound data from each of the elements in the transducer array 200 (i.e. both the central region 212 and the edge regions 214). The processor 116 may generate a group of noise-cancelled signals by removing the estimated electromagnetic noise signal from each of the plurality of signals in the ultrasound data.

Referring to FIGS. 1 and 4, at step 258, the processor 116 beamforms the noise-cancelled signals. At step 260, the processor 116 generates an image from the beam formed noise-cancelled signals. The processor 116 may generate any type of ultrasound image from the noise-cancelled signals. For example, the processor 116 may generate one or more images from the noise-cancelled signals including imaging modes such as: B-mode, Color Doppler, power Doppler, M-mode, and spectral Doppler and the like. The processor 116 may also use the noise-cancelled signals when generating a waveform or calculating a quantitative measurement according to other embodiments. At step 262, the processor 116 displays the image on the display 118.

Figure 5:
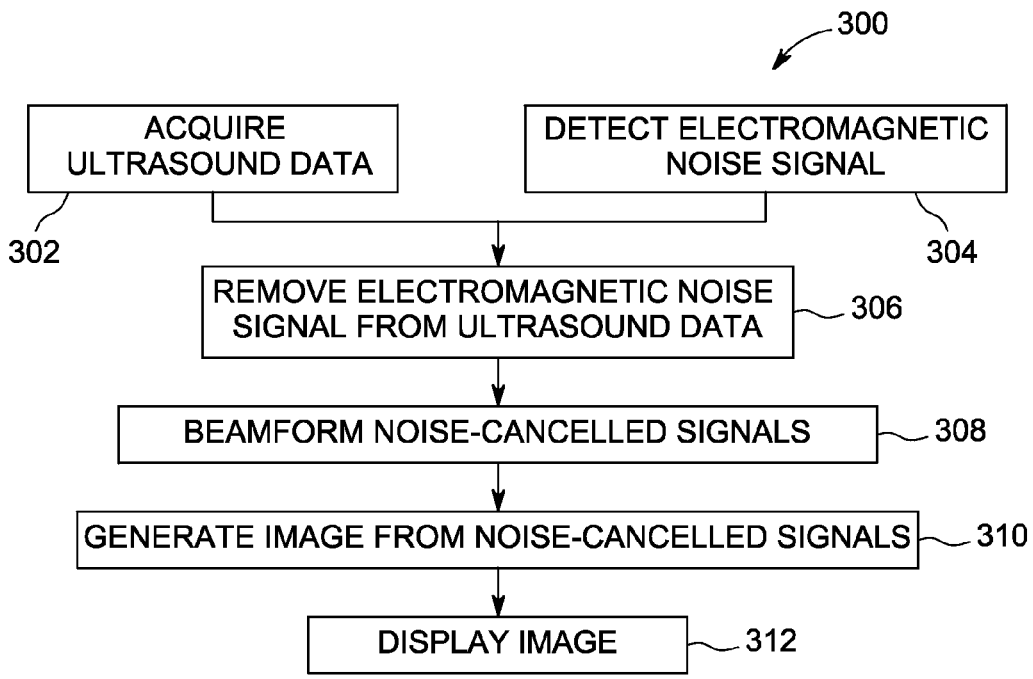
FIG. 5 is a flow chart illustrating a method in accordance with an embodiment.

FIG. 5 is a flow chart illustrating a method 300 in accordance with an embodiment. The method 300 may be implemented with an ultrasound imaging system, such as the ultrasound imaging system 100 (shown in FIG. 1). The individual blocks 302, 304, 306, 308, 310, and 312 represent steps that may be performed in accordance with the method 300. The technical effect of the method 300 is the display of an image from signals with reduced electromagnetic noise.

Referring to both FIG. 5 and FIG. 1, at step 302, the processor 116 controls the transducer array 104 to acquire ultrasound data. According to an embodiment, the ultrasound data may comprise a plurality of signals, one from each of the transducer elements 104. At step 304, the sensor 121 is used to detect an electromagnetic noise signal while the transducer array 104 is acquiring ultrasound data. At step 306, the processor 116 removes the electromagnetic noise signal from each of the plurality of signals of the ultrasound data. For example, the processor may subtract the electromagnetic noise signal from each of the plurality of signals. According to an embodiment, the processor 116 may process the electromagnetic noise signal with one or more of the following: filtering the electromagnetic noise signal, scaling the electromagnetic noise signal, and applying a phase delay to the electromagnetic noise signal. Other processing steps may be applied to the electromagnetic noise signal according to additional embodiments. By removing the electromagnetic noise signals from the ultrasound data, the processor 116 generates multiple noise-cancelled signals from the ultrasound data.

At step 308, the processor 116 beamforms the noise-cancelled signals. The beamforming may be similar to standard receive beamforming except that noise cancelled signals are used for the input. At step 310, the processor 116 generates an image from the beamformed noise-cancelled signals. Then, at step 312, the processor 116 displays the image on the display 118.

Figure 6:
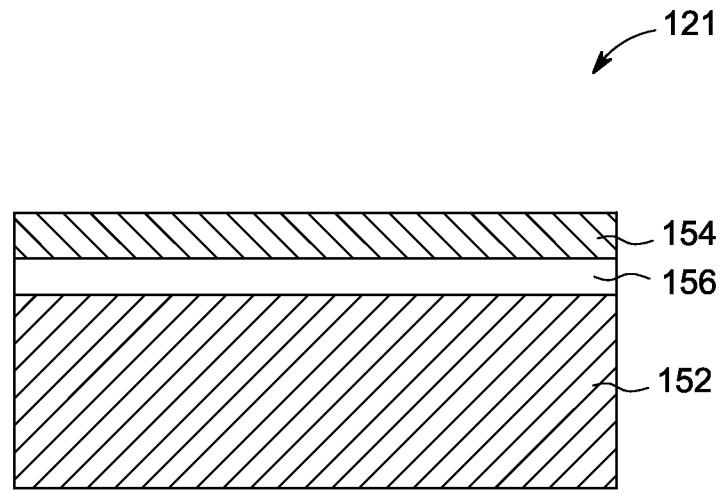
FIG. 6 is a schematic representation of a sensor in accordance with an embodiment.

FIG. 6 is a detailed schematic representation of the sensor 121 shown in FIG. 1. The sensor 121 includes a transducer element 152, that is similar in size and material to the transducer elements used in the transducer array 104 (shown in FIG. 1). According to an embodiment, the transducer element 152 may comprise a piezoelectric material such as Lead zirconate titanate. The sensor 121 also includes a top layer 154 and a gas layer 156. The top layer 154 is constructed of a material that is substantially permeable by electromagnetic radiation. For example, according to an embodiment, materials that are commonly used for the lens of an ultrasound probe, such as RTV60 or KE772U, may be used for the top layer 154 of the sensor. Other materials may be selected as long as they do not substantially attenuate electromagnetic energy. The gas layer 156 serves to shield the transducer element 152 from ultrasound energy since sound waves are substantially reflected due to the acoustic impedance difference between the gas and the piezoelectric material. According to other embodiments, the gas layer 156 may be replaced with any other material which has a significantly different acoustic impedance from the piezoelectric material. The sensor 121 is designed so that the transducer element 152 detects any background electromagnetic noise while the gas layer 156 blocks any ultrasound energy reflected from the patient being imaged. The transducer element 152 responds to electromagnetic noise just like any of the other transducer elements in the transducer array 106 (shown in FIG. 1). The sensor 121 may be sensitive to both coherent electromagnetic noise and incoherent electromagnetic noise.

Figure 7:
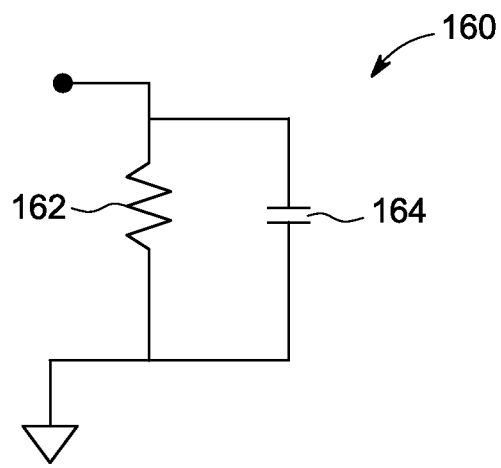
FIG. 7 is a schematic representation of a sensor in accordance with an embodiment.

FIG. 7 is a schematic representation of a sensor 160 that could be used in place of the sensor 121 according to an embodiment. The sensor 160 includes a resistor 162 and a capacitor 164. The resistor 162 and the capacitor 164 are connected in an RC circuit designed to have an electrical impedance similar to that of a transducer element in the transducer array 148 (shown in FIG. 6). According to an embodiment, the resistor 162 may have a resistance of approximately 200 Ohm and the capacitor 164 may have a capacitance of approximately 230 pF. Those skilled in the art should appreciate that it is possible to design many different electrical circuits with the very similar electrical impedances and that the values for the resistor 162 and the capacitor 164 are simply the values according to one exemplary embodiment. It should be appreciated that according to other embodiments, multiple capacitive elements and/or multiple resistive elements may be used to create a circuit with a similar electrical impedance. Additionally, it may be possible to design other types of circuits that would behave similarly when in the presence of electromagnetic noise. The sensor 160 is designed to approximate the electrical impedance of a transducer element 104 (shown in FIG. 1). The sensor 160, however, is not sensitive to ultrasound energy. Therefore, it is possible to use the signal from the sensor 160 as an estimate of the electromagnetic noise signal that would be affecting the other transducer elements in the transducer array 148.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

We claim:

1. A method of ultrasound imaging comprising:
   acquiring ultrasound data with a plurality of transducer elements, the ultrasound data comprising a plurality of signals, the ultrasound data comprising phase information;
   analyzing the ultrasound data to determine an estimated electromagnetic noise signal, wherein said analyzing the ultrasound data to determine the estimated electromagnetic noise signal comprises determining the estimated electromagnetic signal by averaging a subset of the plurality of signals that includes signals from different transducer elements of the plurality of transducer elements, wherein the subset of the plurality of signals is a group of signals originating from a plurality of the transducer elements that are located in one or more edge regions of a transducer array;
   modifying the plurality of signals based on the estimated electromagnetic noise signal to generate a plurality of noise-cancelled signals, the plurality of noise-cancelled signals containing less electromagnetic noise than the plurality of signals; and
   generating an image using the plurality of noise-cancelled signals.

2. The method of claim 1, further comprising beamforming the plurality of noise-cancelled signals to generate a plurality of beamformed signals.

3. The method of claim 2, further comprising using the plurality of beamformed signals to generate the image.

4. The method of claim 1, further comprising displaying the image.

5. The method of claim 1, wherein said analyzing the ultrasound data comprises processing a subset of the plurality of signals.

6. The method of claim 1, wherein said modifying the plurality of signals comprises subtracting the estimated electromagnetic noise signal from the ultrasound data.

7. The method of claim 6, wherein said modifying the plurality of signals comprises processing the estimated electromagnetic noise signal by at least one of filtering the electromagnetic noise signal, scaling the electromagnetic noise signal, or applying a phase delay to the electromagnetic noise signal, said subtracting the estimated electromagnetic noise signal comprising subtracting the processed estimated electromagnetic noise signal from the ultrasound data.

8. The method of claim 1, wherein said analyzing the ultrasound data to determine the estimated electromagnetic noise signal comprises determining the estimated electromagnetic noise signal by cross-correlating signals of the plurality of signals that are from different transducer elements of the plurality of transducer elements.

9. The method of claim 1, wherein said analyzing the ultrasound data to determine the estimated electromagnetic noise signal comprises determining the estimated electromagnetic noise signal by cross-correlating a subset of the plurality of signals that includes signals from different transducer elements of the plurality of transducer elements, the subset of the plurality of signals being signals that originate from a plurality of the transducer elements that are located in one or more edge regions of an array of the plurality of transducer elements.

10. The method of claim 1, wherein said modifying the plurality of signals comprises subtracting the estimated electromagnetic noise signal from signals of the plurality of signals that originate from a plurality of the transducer elements that are located in one or more edge regions of an array of the plurality of transducer elements, and wherein said modifying the plurality of signals comprises subtracting the estimated electromagnetic noise signal from signals of the plurality of signals that originate from a plurality of the transducer elements that are located in one or more central regions of the array of the plurality of transducer elements.

11. The method of claim 1, wherein said modifying the plurality of signals comprises subtracting the estimated electromagnetic noise signal from each of the plurality of signals of the ultrasound data.

12. A method of ultrasound imaging comprising:
    acquiring ultrasound data with a plurality of transducer elements, the ultrasound data comprising a plurality of signals originating from corresponding transducer elements, the plurality of signals comprising phase information;
    determining an estimated electromagnetic noise signal by cross-correlating a subset of the plurality of signals that includes signals from different transducer elements of the plurality of transducer elements, wherein said cross-correlating a subset of the plurality of signals that are from different transducer elements of the plurality of transducer elements comprises cross-correlating signals originating from a plurality of the transducer elements that are located in one or more edge regions of an array of the plurality of transducer elements;
    subtracting the estimated electromagnetic noise signal from the ultrasound data to generate a plurality of noise-cancelled signals, the plurality of noise-cancelled signals containing less electromagnetic noise than the plurality of signals; and
    generating an image using the plurality of noise-cancelled signals.

13. The method of claim 12, wherein said subtracting the estimated electromagnetic noise signal from the ultrasound data comprises subtracting the estimated electromagnetic noise signal from each of the plurality of signals of the ultrasound data.

14. The method of claim 12, wherein said subtracting the estimated electromagnetic noise signal from the ultrasound data comprises subtracting the estimated electromagnetic noise signal from signals of the plurality of signals that originate from a plurality of the transducer elements that are located in one or more edge regions of an array of the plurality of transducer elements, and wherein said subtracting the estimated electromagnetic noise signal from the ultrasound data comprises subtracting the estimated electromagnetic noise signal from signals of the plurality of signals that originate from a plurality of the transducer elements that are located in one or more central regions of the array of the plurality of transducer elements.

15. A method of ultrasound imaging comprising:
    acquiring ultrasound data with a plurality of transducer elements, the ultrasound data comprising a plurality of signals originating from corresponding transducer elements, the plurality of signals comprising phase information;

determining an estimated electromagnetic noise signal by cross-correlating a subset of the plurality of signals that includes signals from different transducer elements of the plurality of transducer elements, the subset of the plurality of signals being signals that originate from a plurality of the transducer elements that are located in one or more edge regions of an array of the plurality of transducer elements;

subtracting the estimated electromagnetic noise signal from the ultrasound data to generate a plurality of noise-cancelled signals, the plurality of noise-cancelled signals containing less electromagnetic noise than the plurality of signals; and generating an image using the plurality of noise-cancelled signals.

16. The method of claim 15, wherein said determining the estimated electromagnetic noise signal by cross-correlating comprises averaging the sub-set of the plurality of signals.

17. The method of claim 15, wherein said subtracting the estimated electromagnetic noise signal from the ultrasound data comprises subtracting the estimated electromagnetic noise signal from the subset of the plurality of signals, and wherein said subtracting the estimated electromagnetic noise signal from the ultrasound data comprises subtracting the estimated electromagnetic noise signal from signals of the plurality of signals that originate from a plurality of the transducer elements that are located in one or more central regions of the array of the plurality of transducer elements.

18. The method of claim 15, wherein said subtracting the estimated electromagnetic noise signal from the ultrasound data comprises subtracting the estimated electromagnetic noise signal from each of the plurality of signals of the ultrasound data.

* * * * *